United States Patent [19]

Gallina

[11] Patent Number: 5,679,655
[45] Date of Patent: Oct. 21, 1997

[54] METHOD OF TREATING LESIONS RESULTING FROM GENITAL HERPES WITH HYALURONIC ACID-UREA PHARMACEUTICAL COMPOSITIONS

[75] Inventor: Damian J. Gallina, Erie, Pa.

[73] Assignee: Patent Biopharmaceutics, Inc., Erie, Pa.

[21] Appl. No.: 471,323

[22] Filed: Jun. 2, 1995

Related U.S. Application Data

[62] Division of Ser. No. 101,826, Aug. 4, 1993.

[51] Int. Cl.$^6$ .................................................. A61K 31/715
[52] U.S. Cl. ........................ 514/54; 514/588; 514/882; 514/912; 514/934; 514/944; 514/966; 536/55.1
[58] Field of Search ............................ 514/54, 588, 882, 514/912, 934, 944, 966; 536/55.1

[56] References Cited

U.S. PATENT DOCUMENTS

| | | | |
|---|---|---|---|
| 4,424,232 | 1/1984 | Parkinson | 514/588 |
| 4,518,583 | 5/1985 | Gallina | 514/588 |
| 4,657,901 | 4/1987 | Ueda | 514/171 |
| 4,872,867 | 10/1989 | Joh | 604/269 |
| 4,900,550 | 2/1990 | Lowry | 424/195.1 |
| 4,957,744 | 9/1990 | Della Valle | 514/54 |
| 5,045,559 | 9/1991 | Scott | 514/423 |
| 5,084,270 | 1/1992 | Claudelli | 424/59 |
| 5,128,326 | 7/1992 | Balazs | 514/54 |
| 5,166,331 | 11/1992 | della Valle et al. | 536/55.1 |
| 5,234,914 | 8/1993 | Gallina | 514/54 |
| 5,240,710 | 8/1993 | Bar-Shalom | 424/422 |
| 5,442,053 | 8/1995 | della Valle et al. | 536/55.1 |

FOREIGN PATENT DOCUMENTS

| | | |
|---|---|---|
| 59-134706 | 8/1984 | Japan . |
| 61-180705 | 8/1986 | Japan . |
| 62-004764 | 1/1987 | Japan . |
| 63-129991 | 6/1988 | Japan . |
| 4-134036 | 9/1990 | Japan . |
| 03291207 | 12/1991 | Japan . |
| 4029934 | 1/1992 | Japan . |
| 2151244 | 7/1985 | United Kingdom . |

OTHER PUBLICATIONS

Japanese Abstract JP 59134706, Pub. Aug. 2, 1984, Koba.
Japanese Abstract JP 62004764, Pub. Jan. 10, 1987, Shiseido.
Japanese Abstract JP 63129991, Pub. Jun. 2, 1988, Denki Kogyo KK.
Japanese Abstract JP 4134036, Pub. Sep. 21, 1990, Meiji Kaisha.
Japanese Abstract JP 03291207, Pub. Dec. 20, 1991, Tsuchiya et al.
Japanese Abstract JP 4029934, Pub. Jan. 31, 1992, Umeda S.
Dissertation Abstracts International, vol. 45/01-B, by James Gailit, 1983.
Derwent Abs. 86-180705 Ozawa et al J61180705 Aug. 1995.
Derwent Abs. 85-075406 Hachiman et al J60075406 Ap. 1985.
Chem. Abs. 106:201531e vol. 106 (1987) Hakamata et al "HIFV" 1986 28(5) 71525.

*Primary Examiner*—Herbert J. Lilling
*Attorney, Agent, or Firm*—Cushman Darby & Cushman

[57] ABSTRACT

This invention includes a pharmaceutical composition including a pharmaceutically acceptable carrier, urea, and hyaluronic acid or a pharmaceutically salt thereof. The invention also includes a method of treating disease of the cutis which includes applying to cutis tissues in need of such treatment a therapeutically effective amount of a composition comprising a pharmaceutically acceptable carrier, urea, and hyaluronic acid or a pharmaceutically acceptable salt thereof, said disease having symptoms selected from the group consisting of inflammation, erythema, edema, papules, vesicles, macules, pustules, scaling, cracking, crusting, and lesions. The invention further includes methods for the treatment of psoriasis, eczema, dermatitis, herpetic conditions, acne, skin ulcers, genital herpes lesions and anorectal disease, which includes applying to tissues in need of such treatment a therapeutically effective amount of a composition including a pharmaceutically acceptable carrier, urea and hyaluronic acid or a pharmaceutically acceptable salt thereof.

8 Claims, 6 Drawing Sheets

METHOD OF TREATING LESIONS RESULTING FROM GENITAL HERPES WITH HYALURONIC ACID-UREA PHARMACEUTICAL COMPOSITIONS

This application is a divisional of Ser. No. 08/101,826 filed Aug. 4, 1993.

BACKGROUND OF THE INVENTION

The present invention concerns pharmaceutical compositions which include urea and hyaluronic acid or derivatives of hyaluronic acid. The present invention further concerns methods of treating disease of the cutis, anorectal epithelium and rectal mucosa employing the aforementioned compositions. The treated disease of the cutis exhibits symptoms such as erythema, edema, inflammation, papules, vesicles, pustules, macules, scaling, crusting, cracking, and/or lesions. Such disease would include psoriasis, eczema, dermatitis, herpetic conditions and acne. Disease of the anorectal epithelium and rectal mucosa exhibits symptoms such as inflammation, cracking, burning, irritation, tenderness, pain, soreness and itching.

The hyaluronic acid-urea preparations are topically applied as skin, anorectal epithelium and anorectal mucosa bonding and adhesion agents, anti-inflammatory agents and bio-repair materials. The use of the hyaluronic acid-urea preparations reduce the inflammation, pain, itching, swelling, and sequelae of the skin, anorectal epithelium and rectal mucosa disease while adhering to and protecting the skin, anorectal epithelium and rectal mucosa tissues.

The composition of the present invention includes two principle components: 1) hyaluronic acid and derivatives thereof; and 2) urea. The derivatives of hyaluronic acid include any pharmaceutically acceptable salt form, for example sodium hyaluronate.

The source of the hyaluronate used in the present pharmaceutical compositions may be a hyaluronic acid or any acceptable salt form of hyaluronic acid. The term "hyaluronate" is often used to mean "hyaluronic acid equivalent" which equates to hyaluronic acid of varying molecular weights and any of their salt forms.

Hyaluronic acid is a naturally occurring mucopolysaccharide with a molecular weight generally ranging between about 50,000 and 8,000,000 (or possibly higher), depending on the source of the material and the analytical methods used in its determination.

Methods of obtaining highly-pure or ultra-pure hyaluronic acid and its salt forms, isolation techniques, and analytical methods for testing purity are provided, for example, in the U.S. Pat. Nos. 3,396,081, 4,141,973, 4,517,295, 4,736,024, 4,784,900 and 4,808,576.

Hyaluronic acid is a linear mucopolysaccharide comprised of alternating glucuronic acid and N-acetyl-glucosamine residues that interact with other proteoglycans to provide stability and elasticity to the extracellular matrix of all tissues. This network of macromolecules regulates tissue hydration and the movement of substances within the interstitial compartment. In resting states most hyaluronic acid is cross-linked with collagen and other high molecular-weight substances, so the concentration of free hyaluronic acid is relatively low. Concentrations of hyaluronic acid are dramatically elevated, however, immediately after tissue injury.

Hyaluronic acid is well known, being found in the joint tissue as well as the vitreous humor of the eyes of mammals. It has been extracted from rooster combs, human umbilical cords and bacterial cultures such as those of hemolytic streptococci groups A and C for various therapeutic purposes. One of the first therapeutic uses of this material was as a replacement for the liquid vitreous of the human eye to aid in ophthalmic surgery, especially in the treatment of retinal detachment. It has also been used for the relief of trauma or irritation in joint tissue of mammals including humans by injection into the synovial fluid of the joint.

Hyaluronic acid and the various salt forms of hyaluronic acid have demonstrated hydrating, lubricating, moisturizing, mechanical, cushioning and wound healing properties.

Commercial hyaluronic acid products, in the United States, include: Viscoat® (Alcon Surgical), Healon® (Pharmacia Opthalmics) and Amvisc® (Lolab).

The second principle component of the present pharmaceutical composition is urea. Urea is represented by the molecular formula $CH_4N_2O$ or $CO(NH_2)_2$. Urea has a molecular weight of 60.06, is freely soluble in water, and has a melting point of 132.7°. Urea is used extensively in the paper industry to soften cellulose. It is also used in fertilizers, animal feeds and ammoniated dentifrices.

Urea is a product of protein metabolism and is the chief nitrogenous constituent of human urine. Urea is a protein denaturant that promotes hydration of keratin and mild keratolysis in dry and hyperkeratotic skin. It is used topically in the treatment of psoriasis, ichthyosis, atopic dermatitis and dry scaly conditions, usually in a 2% to 25% cream or lotion. Urea has long been used as an osmotic diuretic, to promote the healing of infected wounds, and for its antiseptic value.

Commercial medical products containing urea, in the United States, include: Aquacare® (Menley and James), Nutraplus® (Owen/Galderma), Carmol 10®, Carmol 20® and Carmol HC® (Syntex), Gormel Creme® and Gordon's Urea 40%® (GORDON), Lanaphilic® (Medco), Ureacin-10®, Ureacin-20® and Ureacin-40® (Pedinol) and Ultra Mide-25® (Baker Cummins).

Embodiments of the present invention include pharmaceutical compositions comprising urea in an amount of 0.1–40% by weight and hyaluronic acid or pharmaceutically acceptable salts thereof in an amount of 0.05–25% by weight. The compositions of the invention have been made and topically applied to diseased cutis, anorectal epithelium and rectal mucosa to successfully relieve burning, itching, tenderness, pain, soreness and other discomforts. The hyaluronic acid-urea compositions protect tissues of the cutis, anorectal epithelium and rectal mucosa by adhering to them and helping to heal and alleviate disease symptoms.

SUMMARY OF THE INVENTION

The present invention includes compositions comprising urea and hyaluronic acid or its derivatives, and the use of such compositions. In the present compositions, each of hyaluronic acid (or derivatives) and urea is a pharmaceutically active agent. The compositions are used to treat disease of the cutis by topically applying to the cutis tissues, a therapeutically effective amount of the composition. The disease states of the cutis include but are not limited to psoriasis, eczema, dermatitis, herpetic conditions, acne and more generally, disease of the cutis having symptoms of erythema, edema, inflammation, papules, vesicles, macules, pustules, scaling, cracking, crusting, and/or lesions.

The compositions are further used to treat disease of the anorectal epithelium and rectal mucosa by topically applying to such tissues, a therapeutically effective amount of the present compositions. The disease states of the anorectal epithelium and rectal mucosa include but are not limited to rectal fissures and pruritus ani and more generally, disease of the anorectal epithelium and rectal mucosa having symptoms of inflammation, cracking, irritation, soreness, tenderness, burning, pain and itching.

Accordingly, one important object of the present invention is to provide pharmaceutical compositions which include urea and hyaluronic acid or an acceptable salt form of hyaluronic acid which have utility in treating disease of the cutis, anorectal epithelium and rectal mucosa.

Another important object of the present invention is to provide methods for protecting, and promoting the healing of and alleviating the symptoms of diseased cutis, rectal epithelium and rectal mucosa including symptoms of erythema, edema, inflammation, papules, vesicles, macules, pustules, scaling, cracking, crusting and/or lesions, while reducing the associated burning, itching, swelling, irritation, pain, soreness and general discomfort by means of the topical application of the hyaluronic acid-urea composition.

A related object of the present invention is to provide a method of treating disease of the cutis, rectal epithelium and rectal mucosa by utilizing the advantageous bonding and adhering properties as well as the anti-inflammatory, hydrating and healing properties of the hyaluronic acid-urea composition.

Significant Discussion

While a few therapeutic characteristics have been attributed to hyaluronic acid employed alone and urea employed alone, a complete understanding of their independent physiological effect, particularly with respect to the cutis, rectal epithelium and rectal mucosa is not known. Therapeutic compositions containing hyaluronic acid (or derivatives) and urea are not known. Certainly the therapeutic effect of such compositions on disease of the cutis, rectal epithelium and rectal mucosa is not known.

In developing the present invention, clinical investigation has shown that hyaluronic acid or urea aids the therapeutic effect of the other to promote the healing of and alleviate the symptoms of diseased cutis, rectal epithelium and rectal mucosa. In the present invention, hyaluronic acid (or derivatives) is an active pharmaceutical agent and urea is an active pharmaceutical agent. The combination of hyaluronic acid (or derivatives) and urea produces a coordinated or correlated action by the two agents resulting in their therapeutic effect being greater then the sum of the therapeutic effect of each agent taken separately. Present clinical investigation has shown the active agents of the present composition to have a synergistic therapeutic effect.

Thus, the present new combination of hyaluronic acid (or derivatives) and urea produces a surprisingly efficacious therapeutic effect in the treatment of disease of the cutis, rectal epithelium and rectal mucosa.

DETAILED DESCRIPTION OF THE INVENTION AND SOME PREFERRED EMBODIMENTS

To accomplish some of the above described objects of the present invention, one embodiment of the invention is pharmaceutical compositions which include urea and hyaluronic acid or pharmaceutically acceptable salts thereof.

An embodiment of the present invention is the use of hyaluronic acid (or its salts) with urea to employ their combined therapeutic effects in the treatment of disease of the cutis.

Another embodiment of the present invention is to employ the present compositions with particular respect to the property of hyaluronic acid and its derivatives to bond or strongly adhere to cutis tissues, in methods of treatment which provide a protective coating on the irritated, inflamed, burning and/or itching tissues.

A further embodiment of the present invention is to employ the combined therapeutic effect of hyaluronic acid (or acceptable salts) and urea to promote the healing of disease of the cutis having symptoms of erythema, edema, papules, inflammation, vesicles, macules, scaling, pustules, cracking, crusting and lesions.

Additional embodiments of the present invention include: (1) treatment of psoriasis; (2) treatment of eczema; (3) treatment of dermatitis; (4) treatment of herpetic conditions; (5) treatment of acne and (6) treatment of skin ulcers.

Another embodiment of the present invention includes the treatment of disease of the rectal epithelium and rectal mucosa including anorectal disease having symptoms of cracking, inflammation, irritation, soreness, burning, tenderness, pain, and itching.

An important advantage of using hyaluronate for cutis treatment is that while sodium hyaluronate, for example, may be compared to hydrocortisone in its anti-inflammatory effect, unlike hydrocortisone or other glucocorticoids, sodium hyaluronate is not catabolic in nature. Hyaluronic acid and its derivatives enhance the anabolic process as opposed to the catabolic process.

Any pharmaceutically acceptable form of hyaluronic acid may be used in the present invention. This application for the most part, however, will be principally concerned with the representative use of the readily available commercial forms of hyaluronate, such as hyaluronic acid, the potassium salt of hyaluronic acid, and more preferably sodium hyaluronate. This in no way limits the forms of hyaluronic acid employed in the present invention.

Hyaluronic acid (or derivatives thereof) and urea may be incorporated into numerous types of gels, creams, ointments, lotions, solids, pastes, salves, powders, liquids, sprays and/or aerosol vehicles. Sterile distilled water alone and simple cream, ointment and gel bases may be employed as carriers of the hyaluronic acid and urea. Examples of bases and suspending vehicles include Fattibase™ (acrylic polymer resin base), Polybase™ (polyethylene glycol base) by Paddock Laboratories, Inc., Minneapolis, Minn. Such pharmaceutically acceptable carriers are readily available for preparing the present formulations and have desirable pH's, melting points, and preservatives.

Additional therapeutic agents may be added to the present formulations as medically indicated, selected from the classes of: keratolytics, surfactants, counter-irritants, humectants, antiseptics, lubricants, astringents, wound healing agents, emulsifiers, wetting agents, additional adhesion/coating protectants, additional anti-inflammatory agents, vasoconstrictors, vasodilators, anticholinergics, corticosteroids (e.g., glucocorticoids) and anesthetics. Preservatives and buffers may also be added.

In its more specific aspects, the present composition includes a pharmaceutically acceptable carrier, urea in an amount of 0.1–40% by weight and hyaluronic acid (or pharmaceutically acceptable salt) in an amount of 0.05–25% by weight. The preferred amount of urea is 0.1–30% by weight and hyaluronic acid (or salt) is 0.05–15% by weight. The more preferable amount is 0.5–30% by weight urea and 0.1–10% by weight hyaluronic acid (or salt). The most preferable amount is 1.0–25% by weight urea and 0.5–5.0% by weight hyaluronic acid (or salts). The aforementioned amounts of hyaluronic acid (or salt) and urea are therapeutically effective in the treatment of disease of the cutis, anorectal epithelium and rectal mucosa.

BRIEF DESCRIPTION OF THE DRAWINGS

Further objects and advantages of the present invention will be better understood by carefully reading the following detailed description of the presently preferred exemplary embodiments in conjunction with the examples and the accompanying drawings, of which.

The invention is demonstrated with reference to the following examples, which are of an illustrative nature only and which are to be construed as non-limiting.

EXAMPLES

INFRARED ABSORBANCE ANALYSIS OF HYALURONIC ACID, SODIUM HYALURONATE, UREA, AND COMBINATIONS

In order to gain a greater knowledge of the combination of hyaluronic acid (and acceptable salts) and urea of the present composition, infrared absorbance analyses were performed for 1) hyaluronic acid; 2) sodium hyaluronate; 3) urea; 4) urea combined with sodium hyaluronate; and 5) urea combined with hyaluronic acid. A comparison of the infrared absorbance analysis of combined sodium hyaluronate or hyaluronic acid and urea with the infrared absorbance analysis of sodium hyaluronate alone or hyaluronic acid alone and urea alone help determine if a new compound is formed by their combination.

A sample of 1% sodium hyaluronate was prepared by combining 0.3030 grams of sodium hyaluronate, lot #1-9070-4, with 30.0011 grams of water-for-injection (WfI), lot 024052. The sample was mixed using coupled syringes. A sample of 1% hyaluronic acid was prepared by adding 0.125 mls 0.1N HCl to 10 mls of the sodium hyaluronate, dropping the pH to 5.03 (i.e. pH 5.0). A sample of 1% Urea was prepared by adding 0.3333 grams Urea to 30.0009 grams of WfI.

A sample of the sodium hyaluronate/urea combination was made by adding 2.5 mls of each together. A sample of the hyaluronic acid/urea combination was made by adding 2.5 mls of each together. The samples were mixed by coupled syringes.

The urea, sodium hyaluronate, hyaluronic acid, and sodium hyaluronate/urea and hyaluronic acid/urea combinations were scanned for absorbance using infrared spectroscopy. Graphs of the scan spectra results are presented in FIGS. 1, 2, 3, 4, 5 and 6.

The infrared (IR) spectra of 1% urea, 1% sodium hyaluronate, 1% hyaluronate @ pH 5.0 (hyaluronic acid), urea+sodium hyaluronate mixture and urea+hyaluronate @ pH 5.0 (hyaluronic acid) mixture provide the following interpretations and conclusions.

Figure 1:
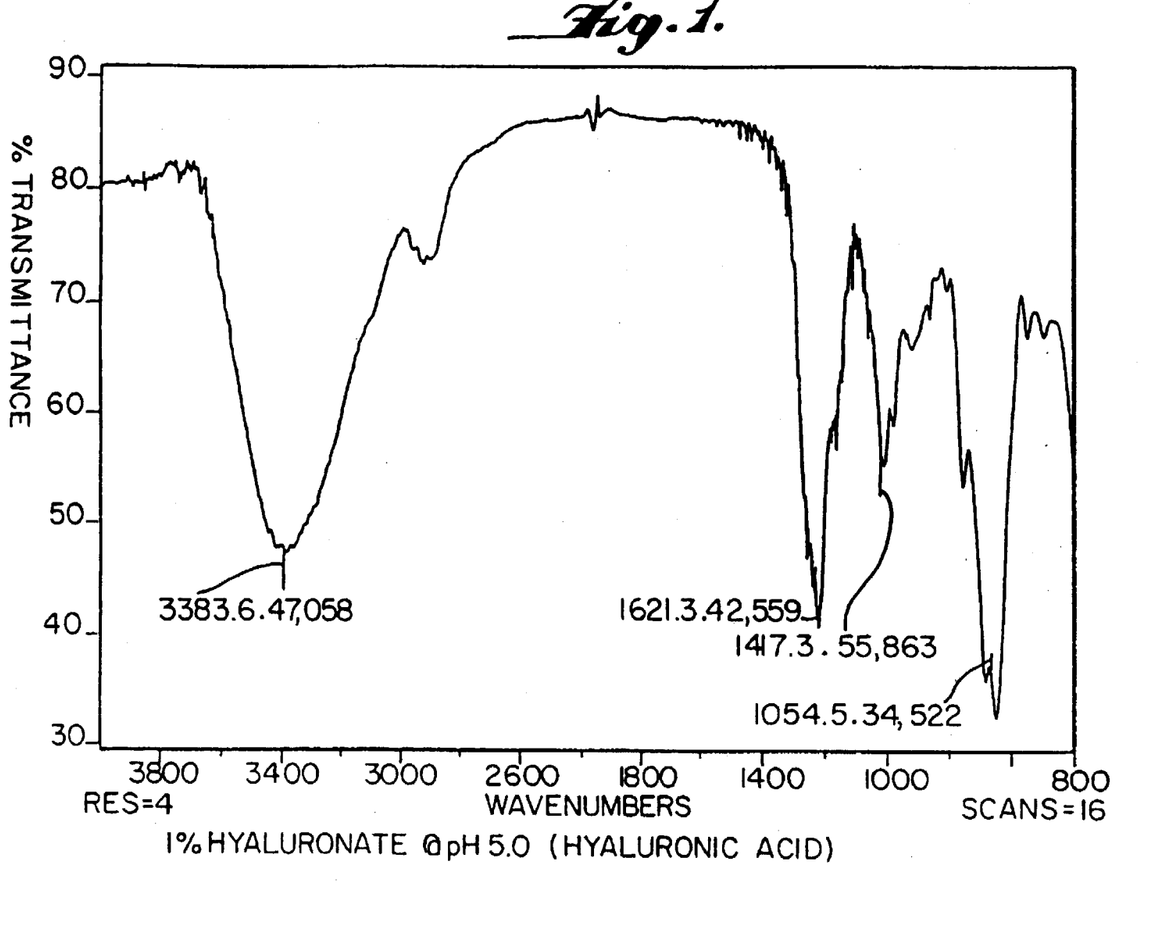
FIG. 1 shows the results of infrared (IR) absorbance analysis of 1% hyaluronic acid.
Figure 2:
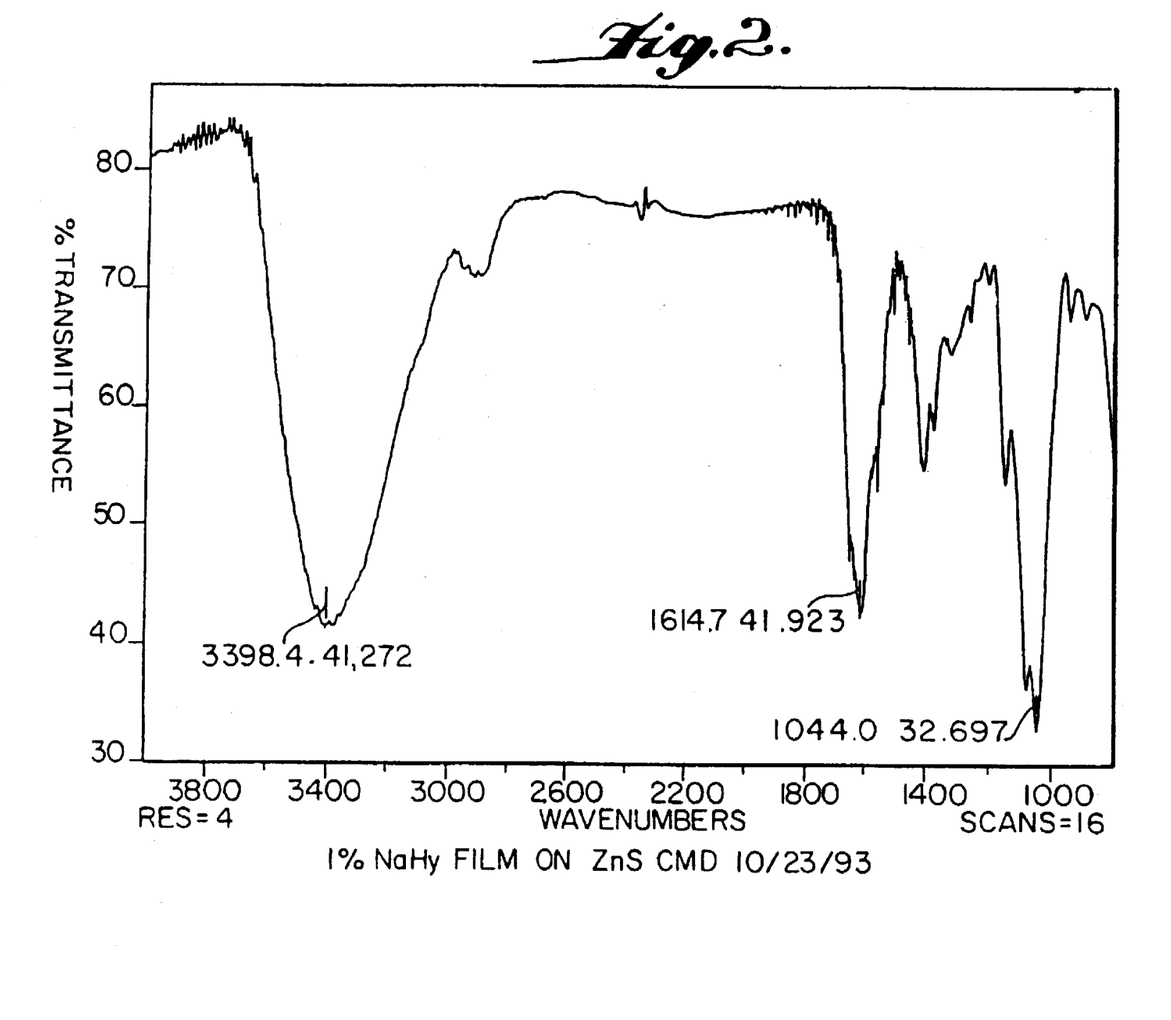
FIG. 2 shows the results of infrared absorbance analysis of 1% sodium hyaluronate (NaHy)

FIGS. 1 and 2 respectively show IR spectra for 1% hyaluronic acid and 1% sodium hyaluronate (NaHy). The spectra for sodium hyaluronate and hyaluronic acid are essentially identical. Note that the 3383 cm−1 band of OH stretches from numerous carboxylic acid and hydroxyl groups and water from the solution. The 1621 cm−1 band is due to the carboxylate anion and water. This is an asymmetrical stretch. A weaker symmetrical stretching band for the same group is at 1417 $cm^{-1}$. The 1054.5 $cm^{-1}$ band is a C—O stretch, ether type, of which there are many in hyaluronic acid.

Figure 3:
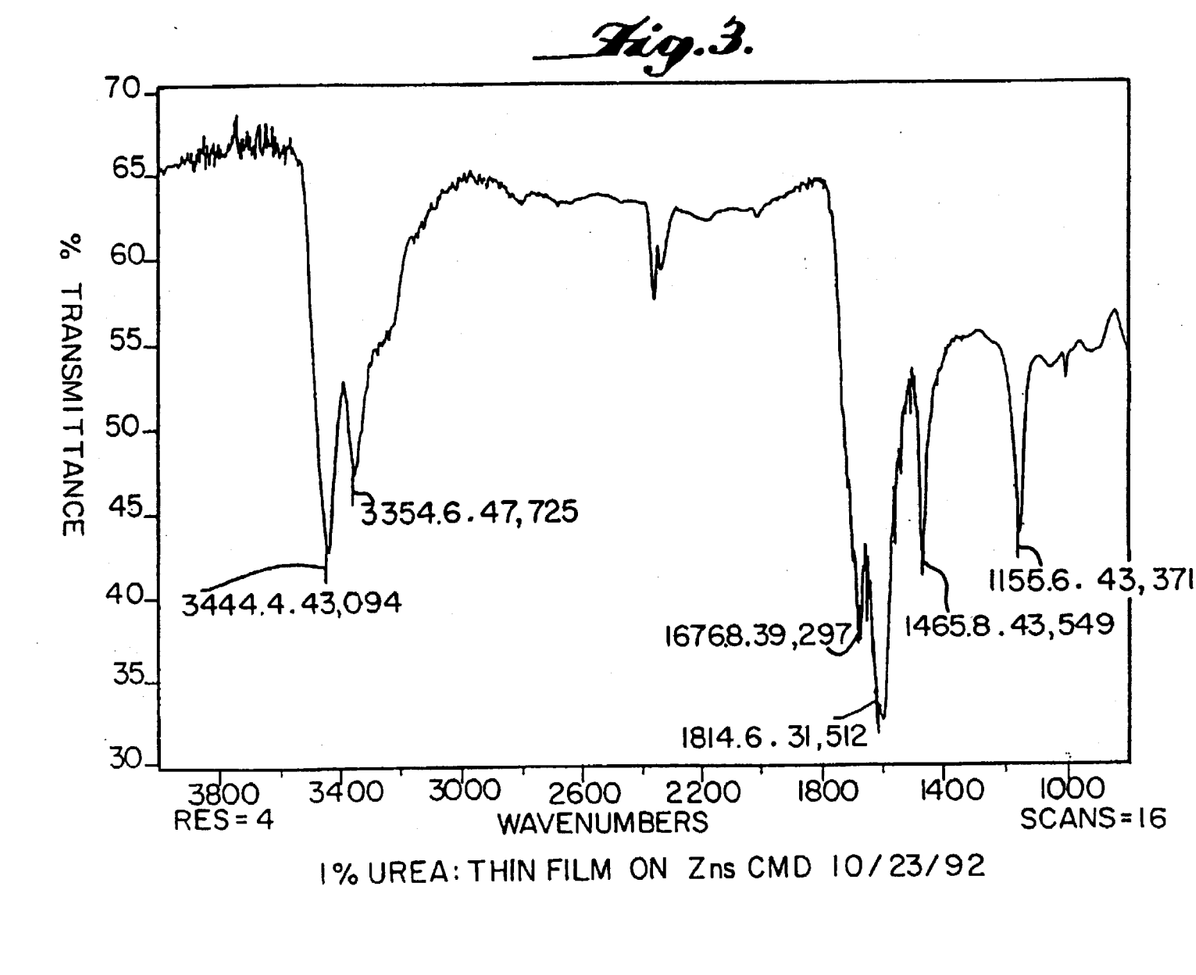
FIG. 3 shows the results of infrared absorbance analysis of 1% urea.

FIG. 3 shows IR spectra for 1% urea. Note that the 3444.4 and 3354 $cm^{-1}$ bands are the NH stretch for hydrogen bonded primary amide with possible interfering OH. The 1676.8 and 1614 $cm^{-1}$ bands are the carbonyl C—O stretch with the amide 1 bands overlapping. Water absorbs at 1620 $cm^{-1}$ and may have interfered here as well. The 1466–1444 $cm^{-1}$ band is the C—N stretch.

Figure 4:
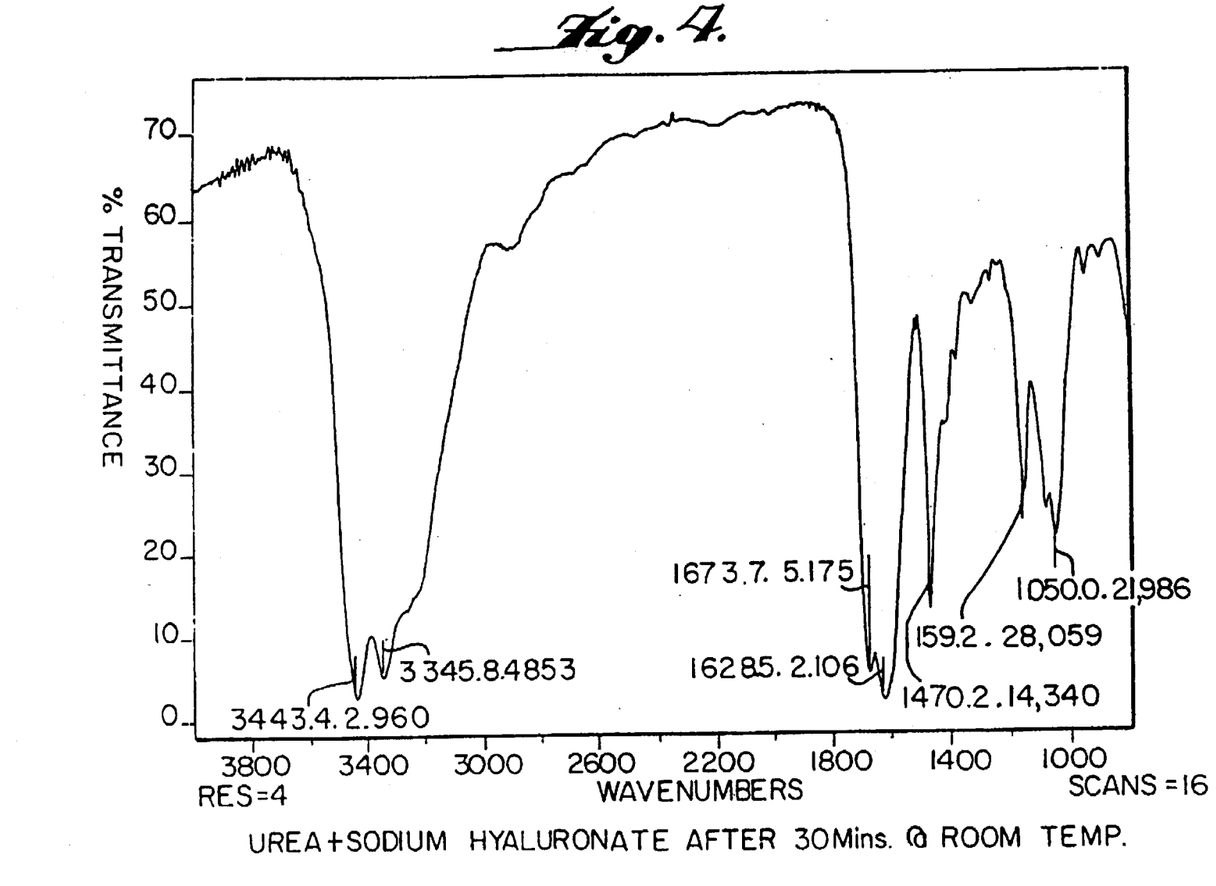
FIG. 4 shows the results of infrared absorbance analysis of a mixture of 1% urea and 1% sodium hyaluronate after 30 minutes.
Figure 5:
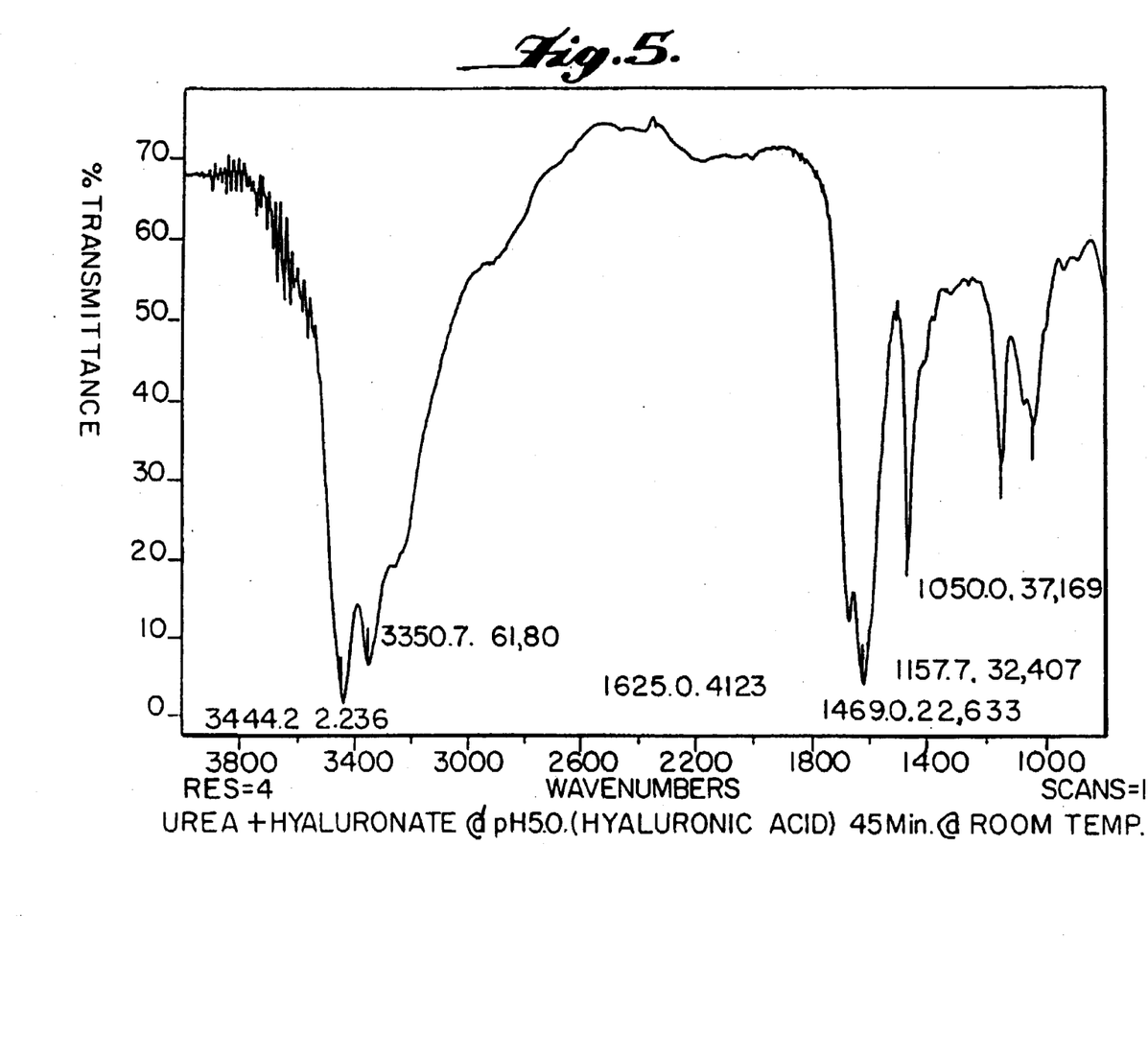
FIG. 5 shows the results of infrared absorbance analysis of a mixture of 1% urea and 1% hyaluronic acid at 45 minutes.

The IR spectrum of the mixtures clearly represents a physical mixture of the two substances. Each band in the mixture spectrum can be attributed to urea or sodium hyaluronate or hyaluronic acid as they appear in their respective IR spectra. Note that the doublet at 2400 $cm^{-1}$ is due to atmospheric carbon dioxide. This is experimental error which probably results from an insufficiently purged IR spectrometer prior to analysis.

Figure 6:
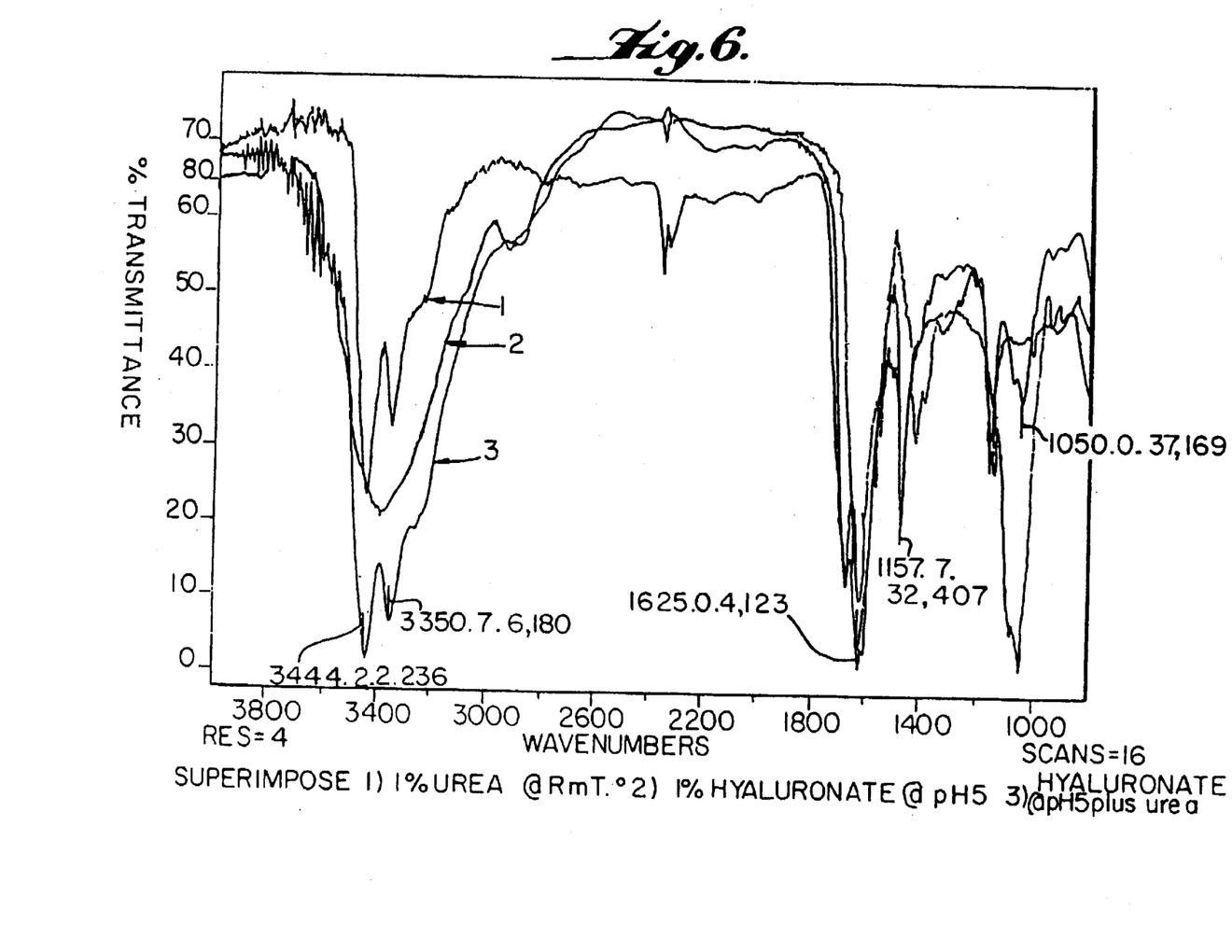
FIG. 6 shows the superimposition of IR absorbance analysis results for 1) 1% urea, 2) 1% hyaluronic acid and 3) 1% urea+1% hyaluronic acid mixture.

FIG. 4 shows IR spectra for 1% urea plus 1% sodium hyaluronate. FIG. 5 shows IR spectra for 1% urea plus 1% hyaluronic acid (hyaluronate @ pH 5.0). A comparison of the spectra of FIG. 1 i.e., hyaluronic acid, FIG. 3 i.e., urea and FIG. 5 i.e., urea plus hyaluronic acid clearly shows that no chemical changes have occurred to the urea and hyaluronic acid when present in combination at the specified pH. A comparison of the spectra in FIG. 2 i.e., sodium hyaluronate, FIG. 3 i.e., urea and FIG. 4 i.e., urea plus sodium hyaluronate shows that no chemical changes have occurred to the urea and sodium hyaluronate in combination at the specified pH. FIG. 6 superimposes the spectra for urea, hyaluronic acid and hyaluronic acid plus urea to facilitate a direct comparison. FIG. 6 helps to confirm the conclusion that no significant chemical change has occurred to the urea and hyaluronic acid when combined together in the composition of the present invention. No chemical reaction has occurred between the urea and hyaluronic acid or urea and sodium hyaluronate.

The fact that the combination of urea and hyaluronic acid (or its salts) do not react to form a new compound, supports the present findings that each of the two pharmaceutically active agents aid the therapeutic effect of each other or that one agent aids the therapeutic effect of the other.

EXEMPLARY COMPOSITIONS

Compositions of the Present Invention

The present hyaluronate-urea preparations may be formulated as a cream, lotion, gel, ointment, solid, paste, salve, powder, liquid, spray and/or aerosol, depending on the ingredients and the amounts employed.

In the following exemplary compositions of the present invention, all liquid measures were converted to the number of grams of liquid used. All solids were dissolved in the appropriate vehicle or melted prior to mixing and blending. All chemical manipulations were performed in a laminar air flow hood. All equipment contacting product or product preparations were sterile and pyrogen free.

Example A)

The following reagents and equipment were used for the preparation of a buffered, pH adjusted, preserved and fragrance added, 1.10% sodium hyaluronate and 2.5% urea lotion:

37% Hydrochloric Acid

Water for Injection (WfI)

Sodium Hyaluronate

Benzyl Alcohol

Methyl Paraben

Sodium Propionate

Sodium Phosphate, Dibasic, Heptahydrate

Sodium Phosphate, Monobasic, Monohydrate

Urea

Fattibase, (Paddock Laboratories)
Glycerin USP
Lecithin
Polyethylene Glycol 4000
Soluble Rose Fluid Extract
Parafilm
Hot Plate
Stir Plate
Magnetic Stir Bar
Standard Laboratory Glassware
Highly Sensitive Balance
Nalgene Containers
pH Meter Reagant Preparation: 1N HCl
1. A 1000 ml volumetric flask was filled with approximately 750 mls of Water for Injection.
2. 96.2 grams of 37% HCl were added to the WfI in the volumetric flask.
   Weight 96.39 gm
3. The flask was covered with parafilm.
4. The flask was inverted several times to mix the contents.
5. An appropriate quantity of WfI was added, sufficient to result in 1,000 mls of solution.

Phosphate Buffered Solution:
1. 22 grams of WfI were weighed and added to a beaker.
   weight 22.0045 gm
2. 3.1372 grams of sodium phosphate dibasic, heptahydrate were weighed and added to the WfI.
   weight 3.1371 gm
3. 7.8628 grams of sodium phosphate monobasic, monohydrate were weighed and added to the WfI.
   weight 7.8626 gm
4. Using a stir plate and magnetic stir bar, the solution was mixed until the contents were dissolved (by visual inspection).
5. The solution pH was measured and recorded.
   pH 5.02
   If the solution pH was not 5.00±0.05, then a new phosphate buffered solution would have been made which would have a pH of 5.00±0.05 using 20 grams of WfI and 10 grams total of phosphates.

Sodium Propionate Solution:
1. 22.0 grams of WfI were weighed and added to a beaker.
   weight 22.0101 gm
2. 20.944 grams of sodium propionate were weighed and added to the WfI.
   weight 20.9441 gm
3. Using a stir plate and magnetic stir bar, the solution was mixed until the contents were dissolved (by visual inspection).
   pH 9.35

Urea Solution:
1. 25.0 grams of WfI were weighed and added to a beaker.
   weight 25.0018 gm
2. 25.0 grams of urea were weighed and added to the WfI.
   weight 25.0012 gm
3. Using a stir plate and magnetic stir bar the solution was mixed until the contents were dissolved (by visual inspection).
   pH 7.43

Lotion Base Water-in-Oil Emulsion:
1. 45.0 grams of fattibase, a homogenous blend of trigylcerides from Palm, Palm Kernel and coconut oils (by Paddock Laboratories), were weighed and added to a beaker.
   weight 45.0011 gm
2. 15.0 grams of PEG 4000 were weighed and added to the fattibase,.
   weight 15.0001 gm
3. 15 grams of Glycerine USP were weighed and added to the same beaker.
4. 15.0 grams of Lecithin were weighed and added to the fattibase, glycerin and PEG4000.
   weight 15.0102 gm
5. 39.0 grams of Soluble Rose Fluid Extract were weighed and added to the beaker.
   weight 39.0120 gm
6. The above ingredients were gently heated on a hot plate to a temperature of not more than 56° C.
7. Using a glass stirring rod, the contents were mixed until all the ingredients melted.
8. The contents were allowed to cool to room temperature with continuous stirring until a firm, stable water-in-oil emulsion resulted.

Procedure:
1. 660 grams of WfI were weighed and added to a 2 liter beaker.
   weight 660.0 gm pH 6.53
2. 22 grams of benzyl alcohol were weighed and added to the beaker.
   weight 22.0400 gm
3. Using a stir plate and magnetic stir bar, the solution was mixed until the contents were dissolved (by visual inspection).
   pH 6.10
4. 1.65 grams of methylparaben were weighed and added to the beaker.
   weight 1.6498 gm
5. Using a stir plate and magnetic stir bar, the solution was mixed until the contents were dissolved (by visual inspection).
   pH 4.40
6. 50.0 grams of urea solution were added to the beaker.
7. Using a stir plate and magnetic stir bar, the combined solutions were thoroughly mixed.
8. 11.0 grams of sodium hyaluronate were weighed and added to the beaker.
   weight 11.0014 gm
9. Using a stir plate and magnetic stir bar, the solution was mixed until the contents were dissolved (by visual inspection). This step was performed overnight. The mixing start and stop times were recorded.
   pH 5.60
10. The solution pH was adjusted to 3.1±0.05 using 1N HCl The amount of 1N HCl used was recorded (in grams) and the final pH was recorded.
    weight 17.1637 gm pH 3.11
11. The solution pH was adjusted to 5.0±0.09 using the sodium propionate solution. The amount of sodium propionate used was recorded (in grams) and the final pH was recorded.
    weight 7.0847 gm pH 4.95
12. The phosphate buffer solution was added to the beaker.
13. A stir plate and magnetic stir bar were used to mix the solution until the contents were dissolved and well mixed (by visual inspection).
    pH 5.54
14. An appropriate weight of WfI and 1N HCl were added to result in 871 grams of solution and a pH of 5.0±0.09. The weight of the WfI and HCl were recorded and the pH was recorded.

| | |
|---|---|
| weight WfI | 62.056 gm |
| weight 1 N HCl | 7.06741 gm |
| pH | 5.08 |
| Total weight of Solution | 871.06 gm |

A hot plate was used to heat the water-in-oil emulsion to a slurry. This slurry was added to the solution, and thoroughly mixed and blended. This resulted in one liter of a buffered, preserved, fragranced and pH adjusted 1.1% sodium hyaluronate and 2.5% urea lotion.

Note that the same or similar methodology of preparation, as set forth in above Example A), was employed in the following compositions of Examples B)–E). Furthermore, numerous preservative, buffering and fragrance systems are readily available and this disclosure is not limited to those mentioned herein. Creams, ointments, lotions, solutions, gels, pastes, salves and spray dosage forms may be derived by varying the amounts of waxes, solids, fats, greases, oils and liquids used in a particular formulation.

Example B)

A 15% sodium hyaluronate and 40% urea highly viscous gel was made by the following method.

1. 45 gm WfI were weighed and added to a beaker
2. 40 gm of urea were weighed and added to the WfI.
3. The contents were thoroughly mixed and dissolved (by visual inspection).
4. 15 gm of sodium hyaluronate were weighed and added to the beaker.
5. The contents were mixed overnight and dissolved (by visual inspection).
6. This resulted in 100 gm of a 15% sodium hyaluronate/40% urea gel.

Example C)

A 40% urea and 0.05% sodium hyaluronate gel was made as follows:

1. 58.95 gm of WfI were weighed and added to a beaker.
2. 40.00 gm of urea were weighed and added to the WfI.
3. The contents were mixed and dissolved (by visual inspection).
4. 0.05 gm (50 mg) of sodium hyaluronate were weighed and added to the beaker.
5. The contents were thoroughly mixed and dissolved (by visual inspection).
6. 1.0 gm Carbopol 940 was weighed and added to the beaker.
7. The solution was mixed until the contents were dissolved (by visual inspection).
8. This resulted in 100 gm of a 40% urea/0.05% sodium hyaluronate gel.

Example D)

A 15% sodium hyaluronate and 0.1% urea cream was prepared as follows:

1. 75.90 gm of WfI was weighed and added to a beaker.
2. 0.10 gm of urea (100 mg) were weighed and added to the WfI and mixed well.
3. 15 gm of sodium hyaluronate were weighed and added to the beaker. The contents were mixed overnight until dissolved (by visual inspection).
4. In a separate beaker 4.5 gm fattibase, 1.5 gm glycerin, 1.5 gm lecithin and 1.5 gm PEG4000 were mixed, melted and then added to the first beaker.
5. The contents of both beakers were thoroughly mixed until well blended. This resulted in a stiff cream formulation.

Example E)

A dilute 0.05% sodium hyaluronate and 0.1% urea cream was made as follows:

1. 84.85 gm WfI were weighed and added to a beaker.
2. 0.1 gm (100 mg) of urea were weighed and added to the WfI.
3. The above were thoroughly mixed.
4. 0.05 gm (50 mg) of sodium hyaluronate were weighed and added to the solution.
5. The above were mixed until dissolved (by visual inspection).
6. 1.5 gm Carbopol 940 were weighed and added to the solution.
7. The above solution was mixed until the contents were dissolved (by visual inspection).
8. 6.75 gm of fattibase, 2.25 gm Lecithin, 2.25 gm Glycerin and 2.25 gm PEG4000 were weighed and added to a separate (second) beaker.
9. The above contents of the second beaker were heated to 55° C.
10. The above contents of the second beaker were continuously melted and stirred to form a slurry.
11. The resulting slurry was added to the solution.
12. The combined contents of both beakers were thoroughly mixed and blended (by visual inspection).
13. This resulted in 100 gm of a 0.05% sodium hyaluronate and 0.1% urea cream formulation.

Example F)

A 1.5% hyaluronate and a 12% urea cream formulation with preservatives was prepared as follows:

| 1. | dissolve: | 2.5 gm benzyl alcohol in 70 gm H$_2$O |
| | add | 5.0 gm sodium propionate |
| | add | 12.0 gm urea |
| | mix & dslv. | 1.5 gm sodium hyaluronate |
| | Subtotal = | 91.0 gm |

2. Next, heat, melt and mix:
 5.0 gm fattibase®
 1.5 gm glycerin U.S.P
 1.5 gm PEG 4000
 1.0 gm Lecithin
3. Add the mixture of step 2 to the solution of above step 1.
4. Results=100 gm 1.5% sodium hyaluronate and 12% urea cream (preparation≦preservatives).

Example G)

A 100 gm sample of a 2.0% urea and a 2.0% hyaluronate lotion was prepared as follows:
 2 gm sodium hyaluronate
 2 gm urea
 4.5 gm fattibase®+87 gm H$_2$O
 1.5 gm lecithin
 1.5 gm glycerine
 1.5 gm PEG 4000
Results=100.00 gm 2% lotion.

Example H)

A 1% hyaluronate and 10% urea cream formulation was prepared as follows.

1 gm NaHy
10 gm Urea
4.5 gm fattibase®
1.0 gm lecithin
1.5 gm glycerin
2.0 gm PEG 4000
80.0 gm H$_2$O Example I)

Urea/sodium hyaluronate preparations may generally be made by adding sodium hyaluronate to a simple urea solution, such as in the following Reference Example VIII. Deduct the number of grams of water for the amount of hyaluronate (grams) to be added. This can be converted into creams, lotions or gels by following the previously mentioned methods. Preservatives and buffer systems may also be added (there are numerous preservatives and buffer systems available for this purpose).

Reference Compositions

Reference Example I)

A viscous aqueous solution of hyaluronic acid, or salt thereof, with gel properties, was prepared by dissolving 5.0% hyaluronate in water. Example:

| 95.00 gm H$_2$O |
| 5.00 gm Sodium Hyaluronate |
| 100.00 gm Total = 5% hyaluronate viscous solution. |

Reference Example II)

In order to enhance gel properties, carbopol, or carbomer, may be added. Preservatives may also be added. Such a formulation was prepared pursuant to the following example:

| | 94.00 gm H$_2$O |
| | 1.00 gm Carbopol 940 |
| | 4.00 gm Sodium Hyaluronate |
| | 0.20 gm methylparaben |
| | 0.10 gm propylparaben |
| | 0.70 gm et. alc. = 4% hyaluronate gel |
| Total | 100 gm |

Reference Example III)

A dilute preparation of hyaluronic acid, or salt thereof, was made pursuant to the following example:

| | 99.90 gm H$_2$OI |
| | .10 gm Sodium hyaluronate |
| Total | 100.00 gm - 0.1% Sodium hyaluronate preparation. |

Reference Example IV)

In general, hyaluronic acid preparations may be made by adjusting the pH (e.g. of sodium hyaluronate). Mineral acids like hydrochloric acid are quite suitable for this purpose and make it relatively easy to achieve the desired pH. Buffer systems may be employed to preserve and protect the desired pH. Sodium phosphate monobasic monohydrate and sodium phosphate dibasic heptahydrate work quite well for this purpose. Sodium propionate and benzyl alcohol are suitable preservatives for this type of preparation.

Example

| | 80.0 gm H$_2$O |
| | 6.0 gm sodium hyaluronate |
| subtotal | 86.0 gm qs ≦ Hcl to desired pH |
| | qs ≦ H$_2$O to 100 gm |
| Result = | 100.0 gm of 6.0% hyaluronic acid formulation. |

Reference Example V)

A 20.0% hyaluronate preparation was made by dissolving 20 gm of sodium hyaluronate in 80 gm of water at room temperature (more than 24 hours may be required to dissolve the hyaluronate).

Reference Example VI)

A 10% Urea solution was made by dissolving 10% Urea in water. Example:

| 10.0 gm Urea |
| 90.0 gm water |
| 100.0 gm total - 10% Urea Solution. |

Reference Example VII)

A 20% urea lotion was prepared by:
1. mixing, heating, and melting
   4.50 gm fattibase®
   1.50 gm glycerin (U.S.P)
   1.50 gm PEG -4000
   1.50 gm Lecithin
2. Adding the above to a solution of 20 gm of urea dissolved in 71 gm of water.

Resulting total=100.00 gm of a 20.0.% urea lotion.

Reference Example VIII)

A 40% urea solution was made by dissolving 40 gm of urea in 60 gm of H$_2$O Result=100 gm of 40% urea solution.

Numerous formulations may be derived by varying the concentrations of the above mentioned ingredients of the above examples and may be determined by the desired characteristics of the finished products. It should also be remembered that other vehicle systems are available for this purpose and therefore this disclosure is not limited to the examples provided.

CLINICAL EVALUATIONS

REFERENCE CLINICAL EVALUATION

A baseline was established setting forth the therapeutic effect of employing a composition containing sodium hyaluronate as the sole pharmaceutically active agent for treatment of disease of the cutis, by performing the following clinical study.

Psoriasis is a chronic skin disorder which affects many patients seen in a dermatologic practice. This study was conducted to determine the efficacy of sodium hyaluronate in the treatment of patients with plague type psoriasis vulgaris.

METHODS

Fifteen patients participated in this study, each with plaque type psoriasis vulgaris. The patients were asked to apply a sodium hyaluronate cream by itself, without other treatment, twice daily to skin lesions. The cream contained 2.0% by weight sodium hyaluronate. The extent of severity of disease ranged from 15% to 40% (rule of nines). This corresponds to body surface area involved. The patients were evaluated at weeks 1 and 2 of treatment as to the extent of improvement. Patients were graded on a scale of 0–4 by the same physician at each treatment visit.

RESULTS

As can be seen by the results shown in Table 1, the effect of the sodium hyaluronate varied from no improvement to moderate improvement (25–50%). Improvement was determined by decrease in redness, scale and thickness of psoriatic lesions. At week 1, the mean improvement level was 0.6. At week 2 the mean improvement level was 0.53 (see scale of improvement on Table 1). At week-2, two patients showed moderate improvement, four patients showed minimal improvement and nine patients showed no improvement. No adverse reactions were noted by the patients.

TABLE 1

RESULTS: PSORIASIS VULGARIS

| Patient | Initial Body % Involved | Week 1 | Week 2 |
|---|---|---|---|
| 1) | 25 | 0 | 0 |
| 2) | 40 | 0 | 0 |
| 3) | 30 | 1 | 0 |
| 4) | 25 | 1 | 1 |
| 5) | 15 | 0 | 0 |
| 6) | 20 | 2 | 1 |
| 7) | 10 | 0 | 1 |
| 8) | 15 | 1 | 0 |
| 9) | 35 | 0 | 0 |
| 10) | 40 | 2 | 2 |
| 11) | 25 | 0 | 0 |
| 12) | 30 | 0 | 1 |
| 13) | 20 | 1 | 0 |
| 14) | 15 | 1 | 2 |
| 15) | 25 | 0 | 0 |

2% Sodium Hyaluronate Cream in Treatment of Psoriasis
Degree of Improvement
0 = No Improvement
1 = Minimal 1–25%
2 = Moderate 25–50%
3 = Good 50–75%
4 = Excellent 75% +

CLINICAL EVALUATIONS OF PRESENT INVENTION

CLINICAL EVALUATION—1

Common skin disorders such as psoriasis, eczema, contact dermatitis and herpetic conditions are seen routinely in a dermatologic office setting. Normally, these conditions have been treated with various topical medications including topical corticosteroids, topical acyclovir and sometimes internal medications such as oral corticosteroids. Patients also tend to treat skin lesions with many over-the-counter medications such as Benadryl cream and Cortaid.

The following was a double-blinded study of 1) hyaluronic acid, 2) urea and 3) combination of sodium hyaluronate with urea in the treatment of various skin disorders.

METHODS

This study entailed 11 patients with a blistering or vesicular type of dermatitis, 8 patients with an eczematous dermatitis and 10 patients with psoriasis. The patients were treated in a double-blinded fashion with either a cream containing (1) 1% sodium hyaluronate plus 4.5% urea, (2) 4.5% urea or (3) 2% hyaluronic acid. The patients were evaluated at weeks 0, 1, 2 and 4 and evaluated as to level of improvement. Level of improvement was evaluated by the same physician (LRF) as to none equals 0, 1 equals minimal or 0 to 25 percent improvement, 2 equals moderate or 25 to 50 percent improvement, 3 equals good or 50 to 75 percent improvement or 4 equals excellent which is greater than 75 percent improvement. The patients were told to use the medication twice daily and to contact the physician if any adverse reactions were noted. At the end of the study period the results were compiled.

RESULTS

The patient results are broken down into three categories. In the vesicular (contact) dermatitis component of the treatment 11 patients were treated. Of these 11 patients 3 were treated with urea, 4 were treated with the combination of sodium hyaluronate plus urea and 3 were treated with urea alone. By week 2 the combination of sodium hyaluronate plus urea had caused the patients to improve between good to excellent. The patients treated with urea improved minimally and the patients treated with hyaluronic acid improved moderately. (See Table 2 and 3)

In the eczema group, 2 of the patients were treated with urea, 3 of the patients were treated with sodium hyaluronate plus urea and 3 were treated with hyaluronic acid. In this group, by week 4, the patients treated with urea had improved moderately. The patients treated with Hyaluronic acid had improved minimally and the patients treated with the combination had improved moderately. (Table 4 and 5)

In the psoriasis group 10 patients were treated; 3 with urea, 3 with the combination medication of sodium hyaluronate with urea and 4 with hyaluronic acid. In this study the urea patients showed minimal improvement, the combination showed minimal improvement and the hyaluronic acid patients showed no improvement at week 4. (See Table 6 and 7)

TABLE 2

RESULTS: CONTACT DERMATITIS (Vesicular)

| Patients | Week 1 | Week 2 | Week 4 | Code |
|---|---|---|---|---|
| 1) | 1 | 2 | N/A | HA |
| 2) | 2 | 3 | N/A | NAHA + Urea |
| 3) | 2 | 3 | N/A | U |
| 4) | 3 | 4 | N/A | NAHA + Urea |
| 5) | 1 | 3 | N/A | HA |
| 6) | 2 | 3 | N/A | NAHA + Urea |
| 7) | 1 | 3 | N/A | HA |
| 8) | 1 | 1 | N/A | U |
| 9) | 2 | 4 | N/A | NAHA + Urea |
| 10) | 0 | 1 | N/A | U |
| 11) | 1 | 3 | N/A | HA |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea

TABLE 3

RESULTS: CONTACT DERMATITIS (Vesicular) MEAN VALUES

| Week | U | HA | NAHA + Urea |
|---|---|---|---|
| 1) | 1 | 1 | 2.25 |
| 2) | 1.67 | 2.75 | 3.5 |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea

TABLE 4

RESULTS: ECZEMA

| Patients | Week 1 | Week 2 | Week 4 | Code |
|---|---|---|---|---|
| 1) | 1 | 2 | 2 | NAHA + Urea |
| 2) | 2 | 2 | 3 | NAHA + Urea |
| 3) | 1 | 0 | 0 | HA |
| 4) | 1 | 1 | 2 | U |
| 5) | 2 | 1 | 2 | U |
| 6) | 1 | 2 | 1 | HA |
| 7) | 0 | 1 | 2 | NAHA + Urea |
| 8) | 0 | 1 | 1 | HA |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea

TABLE 5

RESULTS: ECZEMA MEAN VALUES

| Week | U | HA | NAHA + Urea |
|---|---|---|---|
| 1) | 1.5 | 0.67 | 1 |
| 2) | 1 | 1 | 1.67 |
| 4) | 2 | 0.67 | 2.33 |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea

TABLE 6

RESULTS: PSORIASIS

| Patients | Week 1 | Week 2 | Week 4 | Code |
|---|---|---|---|---|
| 1) | 0 | 1 | 0 | HA |
| 2) | 0 | 1 | 1 | U |
| 3) | 1 | 1 | 1 | U |
| 4) | 1 | 0 | 0 | HA |
| 5) | 0 | 0 | 1 | NAHA + Urea |
| 6) | 0 | 0 | 0 | HA |
| 7) | 0 | 1 | 2 | U |

TABLE 6-continued

RESULTS: PSORIASIS

| Patients | Week 1 | Week 2 | Week 4 | Code |
|---|---|---|---|---|
| 8) | 0 | 1 | 0 | HA |
| 9) | 1 | 2 | 2 | NAHA + Urea |
| 10) | 1 | 1 | 0 | NAHA + Urea |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea

TABLE 7

RESULTS: PSORIASIS MEAN VALUES

| Week | U | HA | NAHA + Urea |
|---|---|---|---|
| 1) | .33 | 0.25 | .67 |
| 2) | 1 | .5 | 1 |
| 3) | 1.33 | 0 | 1 |

Scale
0 - None
1 - Minimal 0–25
2 - Moderate 25–50
3 - Good 50–75
4 - Excellent 75+
HA = Hyaluronic Acid
NAHA = Sodium Hyaluronate
U = Urea Note: the only statistically significant difference was in the vesicular group between the patients treated with the combination of sodium hyaluronate plus urea versus the patients treated with urea alone. Sodium hyaluronate would be useful in the treatment of such vesicular diseases as herpes simplex.

Table 3 shows the mean values of level of improvement for treating contact dermatitis employing urea, hyaluronic acid and combined sodium hyaluronate plus urea for the present study. Using the information in Table 3, the calculated mean level of improvement for urea for both weeks 1 and 2 is 1.33, the mean improvement for hyaluronic acid over weeks 1 and 2 is 1.87 and the mean improvement for combined sodium hyaluronate plus urea over weeks 1 and 2 is 2.87. The combination sodium hyaluronate plus urea shows a 116% increase of effectiveness over urea alone and a 53% increase of effectiveness over hyaluronic acid alone in treating contact dermatitis. The mean level of improvement for values of both urea and hyaluronic acid over the two week period is calculated to be 1.6. The combination of sodium hyaluronate plus urea over two weeks (mean value= 2.87) shows a 79% increase in level of improvement over the two week mean level of improvement for urea and hyaluronic acid (1.6).

Synergism is a phenomenon in which a mixture of two drugs exerts a therapeutic effect which is 1) greater than that exerted by the more active drug acting alone or 2) greater than the additive effect of the two drugs acting independently. The therapeutic effect of sodium hyaluronate is assumed to be equivalent to that of the hyaluronic acid for purposes of this consideration. Based on the foregoing calculations, the combination of sodium hyaluronate plus urea shows a significantly higher level of improvement compared to levels of improvement from employing urea and hyaluronic acid alone and compared to the mean combined level of improvement for urea and hyaluronic acid. This analysis provides evidence of synergistic action by the sodium hyaluronate plus urea composition in treating contact dermatitis.

Based on the mean levels of improvement for treating eczema shown in Table 4, the mean level of improvement for urea over weeks 1–4 is 1.5, the mean level of improvement for hyaluronic acid over weeks 1–4 is 0.78 and the mean level of improvement for combined sodium hyaluronate plus urea over weeks 1–4 is 1.66. The mean level of improvement for combined sodium hyaluronate plus urea is 11% greater then the mean level of improvement for urea alone. The mean level of combined sodium hyaluronate plus urea is 113% greater then the mean level of improvement for hyaluronic acid alone. The calculated mean level of improvement for both urea and hyaluronic acid over weeks 1–4 is 1.14. The mean level of improvement for sodium hyaluronate plus urea (1.66) is 46% greater the mean level of improvement for both urea and hyaluronic acid over weeks 1–4 (1.14). The mean level of improvement of combined sodium hyaluronate plus urea over urea alone and hyaluronic acid alone falls within the definition of synergism as does the level of improvement of combined sodium hyaluronate plus urea over the mean value of urea and hyaluronic acid levels taken together.

Based on the mean values of Table 7 (showing mean values of urea, hyaluronic acid and sodium hyaluronate and combined sodium hyaluronate plus urea in treating psoriasis), the calculated mean value for urea over weeks 1–3 is 0.87, the mean value for hyaluronic acid for weeks 1–3 is 0.25 and the mean value for combined sodium hyaluronate plus urea over weeks 1–3 is 0.89. The mean value of sodium hyaluronate plus urea over 3 the weeks is 2% greater then the mean value for urea over the 3 weeks. The mean value of sodium hyaluronate plus urea over the 3 weeks is 256% greater then the mean value of the sodium hyaluronate over the 3 weeks. The mean level of improvement for both urea and hyaluronic acid over the 3 week period is 0.56. The mean value for sodium hyaluronate plus urea over the 3 weeks is 59% greater then the mean value of urea and hyaluronic acid over the 3 week period. These values show evidence of synergism for the therapeutic effect of combined sodium hyaluronate plus urea.

CLINICAL EVALUATION—2

In the present study compositions containing sodium hyaluronate plus urea (NAHA+UREA) were employed in the treatment of lesions of herpes simplex, psoriasis vulgaris and eczematous dermatitis. The results were compared with the effect of employing compositions containing generic 1% hydrocortisone cream (Revco brand). The purpose of this study was to see if sodium hyaluronate plus urea was more, equal or less efficacious than the widely used over-the-counter medication, hydrocortisone, for the treatment of common dermatologic disorders.

METHODS

In this study the patients were enrolled with paired skin lesions which were similar in appearance. Two patients with herpes simplex labialis, four patients with eczematous dermatitis, five patients with psoriasis vulgaris were treated in this open label study. For each patient one lesion was treated with 1% NAHA+10% Urea and a similar lesion was treated with 1% Hydrocortisone cream. The patients were evaluated at the beginning of the study and then re-evaluated after two weeks of therapy. The patients were graded initially as to the severity of the disease and then at week two they were graded as to the degree of improvement. The patients were evaluated by the same physician at all visits (LFR). The patients were told to apply the appropriate medication to each lesion twice daily and to notify the physician if any adverse reaction occurred. At the end of the study the results were tabulated.

RESULTS

The patients' results are broken down according to the various dermatologic conditions. In the herpes simplex group two patients with paired lesions were treated. By week two, one of the lesions treated with NAHA+Urea had cleared and the other showed only an eschar formation. This was considered marked improvement (See Table 8). In the psoriasis group, two of the five lesions treated with NAHA+Urea showed moderate improvement as compared to similar lesions treated with 1% Hydrocortisone which showed minimal improvement (See Table 9). In the eczematous group of lesions, two of the four lesions treated with NAHA+Urea showed moderate improvement as compared to similar lesions treated with 1% Hydrocortisone cream which showed only minimal improvement. (See Table 10)

In this study, it appears that NAHA+Urea was more effective than generic 1% Hydrocortisone cream. Of great significance is the possible synergistic effect of sodium hyaluronate plus Urea. This may account for the marked improvement in the herpes simplex lesions (vesicular). The synergism might also account for a decrease in hyperkeratotic scale seen in such conditions as psoriasis vulgaris and eczematous dermatitis. This may explain the superior results obtained using the combination of sodium hyaluronate plus urea.

TABLE 8

RESULTS: HERPES SIMPLEX

| Patient | | Week 0 | Week 2 |
| --- | --- | --- | --- |
| 1) | NAHA + UREA | 4 | 1 |
|  | 1% HC cream | 4 | 2 |
| 2) | NAHA + UREA | 4 | 2 |
|  | 1% HC cream | 4 | 3 |

Week 0 & 2 Evaluation
4) Red Grouped Blisters
3) Red Swollen Skin
2) Crusted Eschar
1) Cleared-Normal Skin

TABLE 9

RESULTS: PSORIASIS VULGARIS

| Patient | | Week 0 | Week 2 |
| --- | --- | --- | --- |
| 1) | NAHA + UREA | Mod. | 2 |
|  | 1% HC cream | Mod. | 0 |
| 2) | NAHA + UREA | Min. | 1 |
|  | 1% HC cream | Min. | 0 |
| 3) | NAHA + UREA | Severe | 1 |
|  | 1% HC cream | Severe | 1 |
| 4) | NAHA + UREA | Mod. | 0 |
|  | 1% HC cream | Mod. | 0 |
| 5) | NAHA + UREA | Mod. | 2 |
|  | 1% HC cream | Mod. | 1 |

Week 0 Evaluation
Severe - Red Thick Scale
Moderate - Red Plaque/Minimal Scale
Minimal - Red Skin/No Irritation
Degree of Improvement
0) No Improvement
1) Minimal 1–25%
2) Moderate 25–50%
3) Good 50–75%
4) Excellent 75% +

TABLE 10

RESULTS: ECZEMATOUS DERMATITIS

| Patient | | Week 0 | Week 2 |
|---|---|---|---|
| 1) | NAHA + UREA | Mod. | 2 |
|    | 1% HC cream | Mod. | 1 |
| 2) | NAHA + UREA | Min. | 1 |
|    | 1% HC cream | Min. | 1 |
| 3) | NAHA + UREA | Min. | 2 |
|    | 1% HC cream | Min. | 0 |
| 4) | NAHA + UREA | Mod. | 0 |
|    | 1% HC cream | Mod. | 1 |

Week 0 Evaluation
Severe - Red, Edematous, Micro Vesicles
Moderate - Red Scaly Patch
Minimal - Redness with Scale
Degree of Improvement
0) No Improvement
1) Minimal 1–25%
2) Moderate 25–50%
3) Good 50–75%
4) Excellent 75% +

CLINICAL EVALUATION—3

A 70 year old female with fragile aging skin was suffering from a recalcitrant skin tear of the right thigh. The wound was treated for more than one month using conventional therapy which consisted of: daily cleansing and irrigation, oral and topical antibiotics and regular dressing changes. By the end of the fifth week, day #35, there was no noted improvement.

Beginning on day #36, treatment with a composition containing 0.1% sodium hyaluronate and 1.0% urea was started. This cream preparation was applied to the skin tear three times a day for five consecutive days. At the end of the treatment on the 41st day, minimal improvement was noted. The application of a new formulation comprised of a 0.5% sodium hyaluronate and a 5.0% urea concentration was started on the 42nd day. This second cream formulation was applied to the wound four times a day for one week. The skin tear was completely healed in seven days; 49th day of investigation.

CLINICAL EVALUATION—4

A relatively healthy 65 year old female had periodic scaling, itching and peeling of the little and ring fingers of the left hand and scaling, itching and peeling of the middle and index fingers of the right hand. The problem was diagnosed as an allergic dermatitis of unknown etiology: possibly of contact or food origin. The periodic outbreaks, which typically last two to three weeks, were treated with various topical steroids over a period of several years with moderate to good success.

During one episode the patient applied a 0.05% sodium hyaluronate lotion formulation three to four times a day to the fingers of the left hand and a 2.0% urea lotion formulation to the fingers of the right hand for five consecutive days. At the end of the fifth day, the results were inconsequential; no improvement or relief from itching was noted. A new formula combining 0.05% sodium hyaluronate and 2.0% urea was started on the six day. Again, this new formula was applied three to four times a day for five more days. Accelerated healing was not demonstrated by the end of the 10th day. However, relief from itching was noted almost immediately after the first application.

Several months later following another outbreak, a 1.5% sodium hyaluronate and a 6.0% urea cream formulation was applied to the affected fingers of both hands three to four times a day. Relief from itching was immediate and dramatic improvement was noted by the third day of treatment. Scaling and peeling had ceased and by the fifth day the affected fingers on both hands appeared almost completely normal.

CLINICAL EVALUATION—5

A 78 year old male had a condition in which the skin of both hands was dry, cracked, split and had scale formation; a condition which occured most frequently during the winter months.

During one typical episode, a 20.0% sodium hyaluronate and a 25.0% urea cream formulation was applied three times a day to both hands. This formulation intensely aggravated the problem. Excessive dehydration and keratolysis was obvious and, thus, the formulation was changed on the second day of treatment. The application of a 10.0% sodium hyaluronate gel formulation, without any urea was instituted on the second day of this study. This second gel formulation also produced a drying, dehydrating effect and therapy with this formulation was terminated in two days.

On day five of this investigation, treatment with a 2.0% sodium hyaluronate and 12.0% urea cream formulation was initiated. This 2%/12% cream preparation was applied to the hands three times a day for nine consecutive days. By the ninth day of treatment with this formulation, or the 14th day of the study, both hands appeared extremely well hydrated, softened without scales, significantly improved with diminished cracking and splitting and appeared, overall, well healed. At this point in time, the condition was 90.0% resolved.

CLINICAL EVALUATION—6

A 40 year old woman was taking the drug Accutane® for the treatment of cystic acne. 80% of the cystic acne population treated with Accutane® experience dry, fragile, pruritic skin, a common adverse side effect. To ameliorate this condition, the woman was put on a regimen of applying a combined 2% hyaluronic acid and 15% urea cream formulation, buffered to a slightly acidic pH, three times a day. This 2%/15% formulation greatly reduced the Accutane® induced side effects and proved superior to at least six other commercial products used previously for the relief of this condition.

CLINICAL EVALUATION—7

A 64 year old woman with eczema over the entire body used a 20.0% urea cream preparation, a 2.0% sodium hyaluronate (NaHy) cream preparation and a combination cream preparation comprised of 1.0% sodium hyaluronate and 15.0% urea cream concomitantly three times a day to different areas of her body for three weeks. The woman was evaluated at weeks one, two and three. The results of this study are reported in the following table.

| | Wk. #1 | Wk. #2 | wk. #3 |
|---|---|---|---|
| 20% Urea } | 1 | 1 | 2 |
| 2% Na Hy } | 0 | 0 | 1 |
| 15% Urea + 1% NaHy } | 2 | 3 | 4 |

Key
0 = no improvement
1 = slight improvement
2 = moderate improvement
3 = good improvement
4 = excellent improvement By week four the woman showed excellent improvement by employing the sodium hyaluronate/urea preparation.

The mean level of improvement for the urea preparation over weeks 1–3 was 1.33. The mean level of improvement for the sodium hyaluronate preparation over weeks 1–3 was 0.33. The mean level of improvement for the combination sodium hyaluronate plus urea over weeks 1–3 was 3.0. The mean level of improvement (3.0) for combined sodium hyaluronate plus urea over weeks 1–3 was 125% greater then the mean level of improvement for urea over weeks 1–3 (1.33). The mean level of improvement of combined sodium hyaluronate plus urea over weeks 1–3 (3.0) was 809% greater then the mean level of improvement for sodium hyaluronate over weeks 1–3 ( 0.33 ).

The calculated mean level of improvement for both urea and sodium hyaluronate over weeks 1–3 was 0.66. The mean level of improvement for combined sodium hyaluronate plus urea over weeks 1–3 (3.0) was 354% greater then the mean level of improvement for both urea and sodium hyaluronate over weeks 1–3 (0.66).

The results show a significant increase of therapeutic effect of combined sodium hyaluronate plus urea in treating eczema compared to either urea alone or sodium hyaluronate alone or in considering the mean value of their therapeutic effect over the 3 week period.

CLINICAL EVALUATION—8

In the present study a composition containing sodium hyaluronate plus urea (NAHA+UREA) was employed in the treatment of various ulcers of the skin. Ulcers of the skin including decubitus, diabetic, vascular and AIDS ulcers are commonly seen in a surgical practice. Normally, these ulcers may be treated with debriding agents including saline gauze (wet-to-dry), enzymatics (Elase®, Travase®), whirlpool baths and surgery. Dressing would include semi-occlusive (Op-Site®, Tagaderm®), occlusive (Restore®, DuoDerm®), hydrogel dressing (Intra-Site®, Geliperm®) and saline gauze. Also, anti-infective agents may be used including Bacitracin®, silver sulfadiazine and Mupirocin®. Many times, the above treatments are unsuccessful and ultimately, surgery must be performed.

The following was a double-blinded study of 1) combination of sodium hyaluronate with urea and 2) placebo, in the treatment of various skin ulcers.

METHODS

This study comprised eight (8) Case Studies wherein six (6) AIDS ulcers, one (1) decubitus ulcer and one (1) diabetic ulcer were treated with a cream containing 2% Sodium Hyaluronate plus 0.5% Urea or a placebo cream. The components and preparations of the pharmaceutically active composition (NAHA+UREA) was the following:

| | |
|---|---|
| Sodium Hyaluronate | 2.0% |
| Urea | 0.5% |
| Benzyl Alchol | 2.0% |
| Sodium Propionate | 1.5% |
| Fattibase ® | 6.0% |
| Glycerin | 2.0% |
| Lecithin | 2.0% |
| PEG-4000 | 2.0% |
| WFI | ~80.00%* |
| HCl | ~2.0% |
| | 100.00% |

*(Water for injection) to adjust pH to near normality

The placebo (inactive) formula is identical to the active formula with the exception that 2.50% Carbopol 940 was substituted for the sodium hyaluronate and urea.

The patients were treated in a double-blinded fashion wherein Case Studies 1–4 describe treatment with NAHA+UREA cream and Case Studies 5–8 describe treatment with a placebo cream.

For all Case Studies, a gentle saline wash was performed at the wound site and the cream was topically applied twice a day for up to four (4) weeks. A non-occlusive gauze dressing was applied over the wound site after the application of the cream. The patients were observed frequently by the same physician and photographs were taken. The patients were to notify the physician if any adverse reactions occurred.

RESULTS

The results of this double-blinded study are presented on a case-by-case basis as follows:

CASE STUDY 1

(Treatment with 2% Sodium Hyaluronate plus 0.5% Urea Cream)

In Case Study 1 a 34 year old white male juvenile diabetic was treated. This patient had an ulcer approximately 2.5 cm in diameter, Stage 4, extending through the epidermis, dermis, subcutaneous tissue and down to the periosteum of the lateral malleolus. This ulcer was chronically aggravated by the large brace that the patient wore to assist in ambulation due to instability of his left ankle and overgrowth of bony tissue. The ulcer had been unresponsive to treatment for over three months. The patient had been treated with wet-to-dry saline dressings, Tegaderm®, Duoderm®, Dakin® solution, Bacitracin® ointment and Betadine® wet-to-dry dressings without success. This patient also had undergone a pancreas and kidney transplant and was currently on immunosuppressants and numerous other medications. He suffered from hypertension and took several medications for treatment of that condition. Day 1 showed a 2.5 cm in diameter ulcer over the left lateral malleolus. There was edema and erythema surrounding the ulcer crater. The ulcer extended down through the tissue layers to where one could obviously see the periosteum of the lateral malleolus. Day 10 showed shrinking of the ulcer crater and filling in of subcutaneous tissue in the ulcer bed. There was still some edema and erythema in the surrounding tissue planes. Day 17 showed more narrowing of the ulcer mouth with some closing of the ends of the ulcer with a yellow amber-like eschar. This patient moved away from the study location (out of state) and was unable to come in for a final observation and picture. By telephone he reported that the ulcer had closed completely.

CASE STUDY 2

(Treatment with 2% Sodium Hyaluronate plus 0.5% Urea Cream)

In Case Study 2 a 46 year old black male hypertensive AIDS patient was treated. This patient had two strokes and two episodes of AIDS-related pneumonia. He also had one episode of thrush related to his disease. He had been treated for over four months by surgeons at a local hospital for ulcers of the right lower leg. Debrisan®, Dakin® solution, Betadine® wet-to-dry dressings, saline wet-to-dry dressings, Tegaderm®, Duoderm®, and antibiotic ointments and creams had been utilized to try to heal these ulcers but without success. Day 1 showed the deep ulcer crater was approximately 2.0 cm in diameter and located on the anteromedial aspect of the lower one-third of the lower leg. The skin surrounding the ulcer was hyperpigmented and the ulcer bed was scooped out, containing all layers of the tissue including the epidermis, dermis, subdermal tissue and down to the periosteum of the bone, which would make it a Stage 4 ulcer. Day 7 showed the ulcer decreased in size with filling in of the subdermal tissue with granulation tissue and some eschar formation at the edges. Day 14 showed healthy red granulation tissue with the ulcer decreased in size and totally filled in. Day 28 showed the ulcer healed with an amber-like eschar forming the scab and some areas of new skin and hypopigmented areas around the previous ulcer crater.

CASE STUDY 3

(Treatment with 2% Sodium Hyaluronate plus 0.5% Urea Cream)

In Case Study 3 a 32 year old white hypertensive male with diabetes was treated. This diabetic was not insulin dependent. He did have chronic furuncles and folliculitis along with abscess formation and ulcers of the stasis variety. He had a large approximately 3.5 cm in diameter ulcer of the left posterior thigh in the upper one-third. The ulcer was Stage 3 extending through the dermis, epidermis and subcutaneous tissue. There was a three (3) inch surrounding area of erythema with some edema. There was no active bleeding from the ulcer or the ulcer bed. This patient weighed 648 pounds and had difficulty healing the ulcer due to the effects of pressure and maintaining a dressing over the area. He had been treated with occlusive dressings including Tegaderm®, saline wet-to-dry dressings, Betadine® wet-to-dry dressings, and Bacitracin® ointment. Day 7 showed healing of the ulcer with decrease in the surrounding erythema. It appeared that the ulcer was shrinking with a yellowish-amber eschar. There was granulation tissue over the ulcer bed. Day 16 showed the ulcer healed with an amber-like eschar. The scab was not a typical serosanguinous scab. The erythema had markedly decreased surrounding the ulcer itself.

CASE STUDY 4

(Treatment with 2% Sodium Hyaluronate plus 0.5% Urea Cream)

In Case Study 4 the same patient was treated as in Case Study 2 although a different ulcer was subjected to treatment. Initially there were no thoughts entertained for trying to treat this ulcer because of its large size, irregularity and the patient's history. Treatment was started one week following treatment of the smaller ulcer (of Case Study 2) on the anteromedial aspect of the lower one-third of his lower leg. This Case Study 4 ulcer was 8.0×7.0 cm in a rectangular area over the lower one-third of the anterolateral aspect of his lower leg. This ulcer would be considered as Stage 3 extending through the epidermis and dermis and into the subcutaneous tissue in the subdermal area. Day 1 showed the ulcer with areas involving the subdermal tissue and areas only involving the dermis. The surrounding area was hyperpigmented. There was an island of tissue in the central part of the ulcer that appeared to be fairly normal but hypopigmented. Day 7 showed some filling in of the subdermal areas and some bridging of the tissue on the perimeter of the ulcer with the island in the center. There was some granulation tissue present in several areas of the ulcer bed. Day 21 showed a marked increase in filling in of the tissue from the ulcer rim to the central tissue island with some granulation tissue and some increase in dermal areas. Day 28 showed a marked increase in the dermal tissue and filling in of the areas where the subdermal tissue was exposed. New tissue growth was apparent along with more granulation tissue. The new skin appeared to be hypopigmented but solid and connected to that original central tissue island. At the upper edge of the wound there were some excoriated areas with some clotted blood due to self infliction by the patient. It should be noted that due to patient compliance there were several gaps in terms of two to three days in the patient's treatment regimen. In some areas one could see the yellow-amber scaling that seems to be typical of a healing scab when the ulcer healing was almost complete. The patient thought these areas were "bad tissue" and scratched some of them off.

CASE STUDY 5

(Treatment with Placebo Cream)

In Case Study 5 a 41 year old black male AIDS patient was treated. The patient had one episode of pneumocystic pneumonia that was previously treated. He had a 7.0×9.0 cm. ulcer of the left anteromedial lower leg for six (6) months prior to treatment. The ulcer was a Stage 3 ulcer. The patient stated that he had been treated with Unna boots, silver sulfadiazine cream, antibiotic ointments and currently saline wet-to-dry dressings on an as necessary basis (p.r.n.).

Day 1 showed the large irregular ulcer which was somewhat circular with extension down into the subcutaneous tissue. Day 7 showed no change in the ulcer other than what appeared to be some mechanical debridement along the edges of some of a yellowish exudative material. Day 14 again showed the ulcer with more of the subcutaneous tissue missing but no change in the size of the ulcer in terms of shrinkage. The placebo cream was discontinued after Day 14 due to lack of progress and because of pain experienced by the patient due to the frequent dressing changes.

CASE STUDY 6

(Treatment with Placebo Cream)

In Case Study 6 a 36 year old black male was treated, having an AIDS ulcer on the left lower leg. The patient had an infected 2.0×4.0 cm. ulcer for over four (4) months. He had been treating the ulcer with antibiotic ointment and band-aids for four (4) months. He most currently had used Bacitracin® ointment with a band-aid type covering. He had chronic edema of the lower extremity which caused the extremity to be quite enlarged. The edema was nonpitting and woody in consistency. Day 1 showed the ulcer, which was a Stage 3 ulcer, extending into the dermal layers and the subcutaneous tissue almost down to the muscle. On Day 7 there was no change in the ulcer size and no change in the depth of the ulcer or any filling in of the subcutaneous tissue. The patient discontinued the use of the placebo cream after eight (8) days due to very little improvement in the ulcer.

CASE STUDY 7

(Treatment with Placebo Cream)

In Case Study 7 a 43 year old black male AIDS patient was treated, having a large ulcer of the left forearm involving the elbow region. He did not have any other health problems. He had been treating this ulcer for approximately nine (9) months with daily wet-to-dry dressings. Day 1 showed a 6.0×7.5 cm. ulcer of the left forearm and elbow area. This was a Stage 3 ulcer extending down through the subcutaneous tissue. There was a foul discharge and odor from the ulcer. On Day 7 it appeared that the ulcer was down to the muscle with no decrease in the size of the ulcer or filling in of the defect. The patient discontinued use of the placebo cream after eight (8) days because there was no change in size of the ulcer.

CASE STUDY 8

(Treatment with Placebo Cream)

In Case Study 8 a 56 year old black male drug addict with AIDS was treated. He had been injecting drugs into his arms and legs for over forty (40) years. He suffered from hypertension, but was currently not receiving any treatment. He also had a borderline diabetic condition which had been neglected. He had a large irregular ulcer of the right forearm region with an island of normal tissue in the middle of the ulcer area. The patient stated that the ulcer had been gradually increasing in size despite treatments with Tegaderm®, Duoderm®, Dacon® solution, antibiotic ointments, silver sulfadiazine cream and saline wet-to-dry dressings. Day 1 showed a large butterfly shaped Stage 4 ulcer extending down to the subcutaneous tissue just on top of the muscle. There was no odor or discharge from the ulcer. Day 7 showed no significant change in the ulcer size with no filling in of the defect. The patient discontinued the use of the placebo cream after twelve (12) days because there was no change in the size of the ulcer.

DISCUSSION

The results of Case Studies 1–4 demonstrated that all of the ulcers treated with the cream containing 2% Sodium Hyaluronate plus 0.5% Urea showed dramatic and rapid improvement leading to healing. The use of the NAHA+UREA composition thus provides a significant advancement in the successful treatment of skin ulcers.

The wound healing occurred in much less time than would normally be expected for the stated degree of severity of the various ulcers. Surprisingly, the ulcers healed with a thin serous scab and not the sero-sanguinous scab as expected. In immunocompromised patients such as the diabetic with the pancreas and kidney transplant (Case Study 1) and the AIDS patient (Case Study 2 and 4), the cream was extremely effective without any antibiotic coverage. Those patients treated with the placebo cream exhibited no perceptible improvement and, in fact, in all cases, the ulcers began to worsen within three (3) days after the application of the placebo cream. Consequently, the placebo cream was applied for no more than fourteen (14) days on any of the ulcers that were in the placebo segment of this study. Because of the rapid rate of wound healing, within five (5) days, patients could be identified who were using the NAHA+UREA cream and which patients were using the placebo cream. There were no adverse reactions when using the NAHA+UREA cream. The patients using the NAHA+UREA cream expressed their appreciation of its effectiveness in healing their ulcers when other methods in the past had failed.

CLINICAL EVALUATION—9

In the present study, the same active composition containing sodium hyaluronate plus the urea (NAHA+UREA) as used in Clinical Evaluation—8 was employed in the treatment of various anorectal disease. The NAHA+UREA cream was topically applied to the anorectal epithelium and rectal mucosa. Colon and rectal surgeons and gastroenterologists typically see a large number of anorectal disorders in their practice, including bleeding, irritated hemorrhoids, rectal fissures (either acute or superficial) and pruritus ani.

This study comprised the treatment of three patients, two with pruritus ani and one with a superficial acute rectal fissure. A composition of 2% Sodium Hyaluronate plus 0.5% Urea cream was employed for treatment of these anorectal disorders. All three patients were instructed to topically apply the cream 2-3 times per day in the perianal area and to keep a daily record regarding their symptoms. The patients were initially observed by the physician and at the end of two weeks were finally observed by the physician for evaluation of the treatment.

In all cases, the patients had relief of their symptoms within a range of 3-5 days. All three patients rated the NAHA+UREA cream either good or excellent for relief of their symptoms.

CLINICAL EVALUATION—10

In the present study the same active composition containing sodium hyaluronate plus urea (NAHA+UREA) as used in Clinical Evaluation—8 was employed in the treatment of genital lesions and sores caused by the herpes simplex virus.

The study comprised the treatment of five female patients having moderate lesions caused by herpes simplex virus. Each patient was initially observed by the physician and diagnostic cultures were performed which confirmed that four of the five patients had contracted herpes simplex. Each of the patients had vesicular lesions of the vulva with sharp pain and burning sensations.

A composition of 2% sodium hyaluronate plus 0.5% UREA (NAHA+UREA) cream was employed for treatment of this herpetic disorder. All five patients were instructed to topically apply the cream 3-4 times daily to the lesions. The patients were instructed to keep a daily record on a flow sheet regarding their symptoms. Each patient was further instructed to use soap and water to clean the lesions and dry the area with a hair dryer after washing, twice each day. The patients were to apply the cream for a maximum of four days and each was observed from seven to ten days after initial observation.

The results of the study showed that four of the patients indicated relief of pain within one to three days. One patient indicated no relief of pain within four days. On a scale of 1 to 3, four of the patients rated the cream as a "3" for good relief of pain while the fifth patient rated the cream as a "1" for poor relief of pain. Upon final observation by the physician, all five patients showed no lesions or remnants of lesions.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

I claim:

1. A method of treating lesions resulting from genital herpes which comprises applying to the genital tissues in need of such treatment a therapeutically effective amount of a composition comprising a pharmaceutically acceptable carrier, urea in an amount of 0.1–40% by weight, and hyaluronic acid or a pharmaceutically acceptable salt thereof in an amount of 0.05–25% by weight.

2. The method of claim 1 wherein said composition further includes an additive selected from the group consisting of keratolytics, surfactants, counterirritants, humectants, antiseptics, lubricants, astringents, emulsifiers, wetting agents, wound healing agents, adhesion/coating protectants, vasoconstrictors, anticholinergics, corticosteroids, anesthetics and anti-inflammatory agents.

3. The method of claim 1 wherein said composition is in a form selected from the group consisting of cream, lotion, gel, ointment, solid, paste, salve, powder, liquid, spray and aerosol.

4. The method of claim 1 wherein said carrier is water.

5. The method of claim 1 wherein said pharmaceutically acceptable salt is sodium hyaluronate.

6. The method of claim 1 wherein said composition includes urea in an amount of 0.1–30% by weight and hyaluronic acid or a pharmaceutically acceptable salt thereof in an amount of 0.05–15% by weight.

7. The method of claim 1 wherein said composition includes urea in an amount of 0.5–30% by weight and hyaluronic acid or a pharmaceutically acceptable salt thereof in an amount of 0.1–10% by weight.

8. The method of claim 1 wherein said composition includes urea in an amount of 1.0–25% by weight and hyaluronic acid or a pharmaceutically acceptable salt thereof in an amount of 0.5–5.0% by weight.

* * * * *